(12) United States Patent
Erlebacher (10) Patent No.: US 6,473,640 B1
(45) Date of Patent: Oct. 29, 2002

(54) IMPLANTABLE DEVICE AND METHOD FOR LONG-TERM DETECTION AND MONITORING OF CONGESTIVE HEART FAILURE

(76) Inventor: Jay Erlebacher, 55 Woodland Park Dr., Tenafly, NJ (US) 07670

(*) Notice: Subject to any disclaimer, the term of this patent is extended or adjusted under 35 U.S.C. 154(b) by 0 days.

(21) Appl. No.: 09/488,101
(22) Filed: Jan. 20, 2000

Related U.S. Application Data
(60) Provisional application No. 60/117,078, filed on Jan. 25, 1999.

(51) Int. Cl.[7] ................................................. A61B 5/05
(52) U.S. Cl. ..................................................... 600/547
(58) Field of Search ..................... 607/22, 62; 600/506, 600/547

(56) References Cited

U.S. PATENT DOCUMENTS

| | | | |
|---|---|---|---|
| 5,788,643 A | * | 8/1998 | Feldman ..................... 600/547 |
| 6,253,103 B1 | * | 6/2001 | Baura ......................... 600/547 |
| 6,278,894 B1 | * | 8/2001 | Salo et al. ................... 600/547 |

* cited by examiner

Primary Examiner—William E. Kamm
Assistant Examiner—Jeffrey R. Jastrzab
(74) Attorney, Agent, or Firm—Francis C. Hand; Carella, Byrne et al (57) ABSTRACT

The implantable device for long term monitoring of congestive heart failure employs a signal generator, such as within a pacemaker, to generate an electrical signal which is monitored to obtain a single or dual frequency measurement that can independently measure systemic venous and pulmonary (lung) impedance. The device is able to detect changes in resistance to a flow of current in the systemic venous system and changes in impedance to a flow of current through a lung to thereby indicate separate detection of systemic venous and pulmonary congestion.

20 Claims, 3 Drawing Sheets

IMPLANTABLE DEVICE AND METHOD FOR LONG-TERM DETECTION AND MONITORING OF CONGESTIVE HEART FAILURE

This application claims the benefit of U.S. Provision Application No. 60/117,078, file Jan. 25,1999

BACKGROUND OF THE INVENTION

This invention relates to an implantable device and method for long term detection and monitoring of congestive heart failure. More particularly, this invention relates to a device and method of assessing pulmonary congestive and/or systemic venous congestion.

As is known, congestive heart failure (CHF) in a patient is caused, in part, by a build-up of fluid in the lungs and body of a patient. Typically, the of build-up of fluid in the. lungs and body (i.e. edema) is a sign of failing heart circulation, for example, as described in U.S. Pat. No. 5,876,353. Accordingly, attempts have been made for detecting the occurrence of edema in the lungs, for example, using impedance monitoring. In some cases, proposals have been made to take external or internal measurements of impedance as an index of lung water content (edema). However, suitable results have not been obtained to permit long term monitoring of pulmonary and systemic venous congestion.

By way of example, U.S. Pat. Nos. 5,876,353 and 5,957,861 describe the use of an impedance monitor for discerning edema in a patient through the use of respiratory rate and direct current (DC) impedance. In particular, an impedance and respiratory monitoring circuit is added to a pacemaker system in order to obtain measurements of transthoracic impedance and respiratory rate. These measurements are taken over a long term to obtain a long term average signal so that differences can be used to algorithmically process the variance over time for use to assess the amount of tissue edema over the long term changing condition. However, such techniques fail to distinguish between left heart failure causing lung (pulmonary) edema and right heart failure causing systemic venous congestion. In clinical cases, right and left heart failure may occur in concert or independent of each other. DC impedance in particular is more reflective of systemic venous congestion and may be insensitive for detection of pulmonary edema. Furthermore, respiratory rate changes are a relatively late consequence of CHF and may not occur far enough in advance of dangerous clinical consequences to permit intervention. In addition, respiratory rate changes are not specific to CHF. They occur with exacerbations of various ling diseases such as emphysema, asthma and the like, as well as with anxiety, fever, ascent to high altitudes, and other common conditions.

U.S. Pat. No. 5,282,840 describes a multiple frequency impedance measurement system for monitoring a condition of a patient's body tissue in order to obtain an indication of the condition of the tissue. As described, the measurement system employs a pair of electrodes which are located in contact with the tissue to be monitored. During use, electrode signals are to be applied to the two electrodes at different frequencies with the impedance between the electrodes being measured at the different frequencies. Any changes which occur in the measured impedances over time are then used to indicate changes in tissue condition, such as those induced by ischemia, drug therapies, allograft rejection, lead fractures or insulation degradation. When used with a cardiac pacemaker, the impedance values may be compared over a period of time such as hours, days, weeks or even months and may be employed to provide an increase in minimum or base pacing rate in an attempt to counteract a detected ischemia. The measurement system may also be employed to measure respiration for control of the pacing rate. In this case, one electrode is located within the right ventricle in spaced relation to a can electrode of a pacemaker with a substantial amount of lung tissue located within the sensing field of the electrodes. Changes in the impedance may then be used to calculate a respiration rate.

U.S. Pat. No. 4,676,252 describes a double indicator pulmonary edema measurement system for measuring in vivo extra vascular lung water (pulmonary edema). As described, the detection of pulmonary edema is provided by detecting the response of the pulmonary vascular network to indicator dilution of thermal and conductivity modifiers as a function of not only detected thermal and conductivity value but additional body parameters including blood characteristics and a temperature modifier of conductivity. From these, a value for extra vascular heat capacity is determined from which a quantified lung water measurement is obtained.

U.S. Pat. No. 5,003,980 describes a method and apparatus for measuring lung density by Compton Backscattering.

SUMMARY OF THE INVENTION

It is an object of the invention to provide a relatively simple technique for long term detection and monitoring of right and left sided congestive heart failure.

It is another object of the invention to assess congestive heart failure by measuring bioimpedance with an implant device.

It is another object of the invention to utilize a cardiac pacemaker, defibrillator and/or cardioverter/defibrillator with circuitry for monitoring of congestive heart failure in a patient.

Briefly, the invention provides an implantable device and method for long term monitoring of congestive heart failure. In particular, the invention provides a method of measuring bioimpedance to assess congestive heart failure and particularly lung capacitance as an index of pulmonary congestion.

The invention recognizes that the different bio-electric properties of blood and lung tissue permit separate assessments of systemic venous congestion and pulmonary congestion. That is, the lung has a high resistance to current flow as compared to venous blood with the structure of the lung being similar to a nearly dry sponge. As is known, the lung is a honeycomb of air spaces (i.e. dielectric) surrounded by blood filled capillaries and associated pulmonary arterial and venous vessels (i.e. conductors). Thus, the lung may be modeled as an array of resistors and capacitors which can be simplified to a parallel resistive-capacitive circuit. As the lung becomes congested with edema fluid, its resistance decreases and its capacitance changes as well.

Electrical impedance is a vector quantity. Vector quantities have a scalar magnitude and a direction given as an angle ($\Phi$) to the horizontal. Using trigonometry, a vector can be resolved into its horizontal and vertical components. In the case of electrical impedance, the scalar magnitude of impedance (Z) is given by the Voltage across a circuit divided by the Current through the circuit. The angle ($\Phi$) is the phase angle between the voltage and current. The horizontal or "real" component of impedance is the resistance (R) and the vertical "complex" component of impedance is the reactance (X). Reactance may be due to inductance or capacitance, but in the case of thoracic impedance, reactance is purely capacitive ($X_c$). Capacitive reactance is given by the formula $X_c=1/(2\pi fC)$, where f is the frequency of an alternating sine wave signal, and C is the capacitance.

By measuring the capacitive component of lung impedance, an index can be obtained which is independent of the systemic venous resistane That is, there would be separate indexes of systemic venous congestion and of pulmonary congestion Development of the implantable device is based, in part, on a realization that the blood in the right ventricle and venous system provides the lowest resistance path between an electrode in the heart and an electrode implanted in an upper chest of the patient, usually not far from the subclavian vein. The resistance of this blood path is expected to be much lower than an alternate parallel current path through aerated lung tissue. Thus, the right ventricle and systemic venous system of the upper body are likely to dominate in a resistance measurement where the low resistance of the venous system is in a parallel circuit with the high resistance lung.

With direct current, i.e. a constant unvarying signal with a constant amplitude, the capacitive reactance is infinite, so at DC and very low frequencies, almost all of the current flow is through the blood of the vascular system in general and the systemic venous system in particular. Very little current will flow through the lung because the lung has a much higher resistance than the blood in the systemic venous system. However, at higher frequencies, the capacitive reactance of the lung decreases and may be comparable in magnitude to the systemic venous resistance. A single measurement of impedance and the phase angle allows a computation in a microprocessor using conventional circuitry of the real component of impedance (resistance), which will primarily be due to current flow in the systemic venous system, and the complex component of impedance (capacitive reactance) which will reflect conditions in the lung. The lung will also have a resistive component, but it would be very high so little current will flow there and so can be considered clinically negligible.

This invention takes advantage of the fact that the physical properties of the lungs are such that they have electrical capacitance, and the physical properties of the blood are such that there is little or no capacitance at the frequencies that will be used. By modeling the systemic venous blood as purely resistive, and the lung as at least partially capacitive, one can semi-independently use resistance as an index of systemic venous congestion, and capacitance as an index of pulmonary congestion. This can be done at a single frequency by calculating the complex component (capacitive reactance) and the real component (resistance) from the total impedance and phase angle. Capacitance can be calculated from the capacitive reactance if the frequency of the signal is known.

In parallel circuits, as this model, the calculations are easier if the inverse of the quantities are used. That is to say, admittance is the inverse of impedance, conductance is the inverse of resistance and the complex (imaginary) component of admittance is the inverse of reactance.

There are several ways to measure the capacitive component but the most useful is a dual frequency measurement. In this case, the response of the circuit would be frequency dependent and would give different impedances for a high frequency sine wave versus a long DC pulse. In the event that sine waves are difficult to generate in a pacemaker device, a train of short duration pulses may be generated by the pacemaker instead. Short and long pulse widths should also yield different impedances because of their different frequency content.

For purposes of the invention, the type of high frequency signal which is used to obtain the measurements required is one which has a current whose amplitude varies with a repeating pattern at a specific frequency. This includes sine waves, square waves, truncated exponential waves which are typically the output of a pacemaker and the like.

In one embodiment, use is made of a dual frequency measurement to separate out the systemic venous congestion and the pulmonary (lung) congestion. In this respect, system venous congestion is detected using a low frequency or direct current resistance or conductance measurement of the current path through the blood of a systemic venous system. Pulmonary congestion is detected using a high frequency measurement of complex impedance, complex admittance or capacitance of the lung. As these tissues become congested, the resistance and the complex component of impedance will change and allow separate detection of systemic venous and/or pulmonary congestion.

In this embodiment, the implantable device may include a pair of electrodes which are employed in suitable locations in a patient in order to obtain the desired measurements, and, more particularly the changes in measurements over time, in the systemic venous system and in the lungs as well as a signal generator for emitting an electrical signal to the first electrode. The signal generator may be incorporated in a pacemaker which is implanted into the chest of a patient or may be employed with other implanted devices, such as defibrillators and cardioverter/defibrillators or dedicated solely to the monitoring of a patient for cardiac heart failure (CHF) as a stand-alone device.

The electrodes may be placed in the subcutaneous tissue of the chest or may be surgically implanted inside the chest as in during heart surgery or during implantation of transvenous electrodes, for example in or on the right heart, i.e. in the right ventricle or the right atrium. Also, one electrode may be implanted in the right heart while the second electrode is on the housing for the signal generator or placed elsewhere in the chest to optimize the measurements being made. In any case, a first current path between the electrodes is to be established through the blood of the systemic venous system which includes, for example, but not limited to, the right ventricle, the right atrium, the vena cava, the innominate vein and the subclavian vein. In addition, a second current path between the electrodes is to be established which passes through the lung tissue of the patient, for example from the right atrium to the signal generator or from the right ventricle to the signal generator.

Depending on the impedance offered by the body tissue, the current from the first electrode passes through the first current path extending through the blood of the systemic venous system of the patient and/or the second current path extending through the lung of the patient.

The implantable device also includes a means for measuring the resistance or the conductance to current flow in the first current path as well as for measuring at least one of complex impedance, complex admittance and capacitance in the second current path whereby changes in the measurements of the resistance or conductance are indicative of systemic venous congestion and changes in the measurements of complex impedance, complex admittance or capacitance over a period of time are indicative of pulmonary congestion. In terms of circuitry, the measuring means includes a microprocessor to receive measurements of the current, voltage and the phase angle between the current and voltage passing between the electrodes and to calculate the desired values.

The measuring means also employs means for detecting the current generated by the electrical signal and for emitting a signal indicative of the current flowing through the body of the patient to the microprocessor. An operational amplifier is also provided to amplify the signal for delivery to the microprocessor.

The measuring means also includes a second operational amplifier connected to the electrodes or to a second pair of electrodes for detecting the voltage generated by the electrical signal through the body of the patient and for emitting a corresponding amplified signal to the microprocessor.

The measuring means also includes a phase detector connected to each amplifier to measure the phase angle between the detected voltage and the indicated current.

The microprocessor is connected to the phase detector and to each amplifier to receive values corresponding to the measured phase angle, the detected voltage and the indicated current and to calculate the real and complex components of the impedance of the body tissues based upon the received values. In this respect, a calculated impedance at a direct current (DC) or at a low frequency of the electrical signal from the signal generator is indicative of systemic venous congestion while the calculated complex impedance at a higher frequency of the electrical signal from the signal generator is indicative of pulmonary congestion.

In accordance with the dual frequency measurement method of the invention, a DC signal or an electrical signal of low frequency is passed into both paths. The resistance, in this case, is dominated by the current flowing in the systemic venous system. Thus, the resistance which is measured is indicative of the systemic venous system. Should there be a decrease in measured resistance, this would be indicative of congestion of the systemic venous system.

Subsequently, an electrical signal of higher frequency is passed into the two paths and the complex impedance, complex admittance or capacitance to the current flow of the signal is measured in the second path. Should there be a change in the measured values, this would be indicative of congestion of the lung.

In another embodiment, a single frequency measurement may be used whereby the computed real component of impedance is indicative of systemic venous congestion, and the complex component of impedance, admittance or the capacitance is indicative of pulmonary congestion.

Once the microprocessor has determined that there is congestion in one or the other, or both, of the systemic venous system and the lung, signals may be emitted, for example, to a pacemaker to increase the pacing rate in order to reduce the congestion. Alternatively, the microprocessor may deliver signals to a pacemaker which may pace multiple sites in the left and right ventricle to improve the contraction pattern and function of the heart.

In other cases, the signals received from the microprocessor may also be processed for purposes of administering drugs, changing a dosage rate of drug therapy and the like. In still other cases, signals may be emitted in the form of tones or the like to alert a patient or may be emitted to a remote location to alert medical personnel.

BRIEF DESCRIPTION OF THE DRAWINGS

These and other objects and advantages of the invention will become more apparent from the following detailed description taken in conjunction with the accompanying drawings wherein.

DETAILED DESCRIPTION OF THE PREFERRED EMBODIMENT

Figure 1:
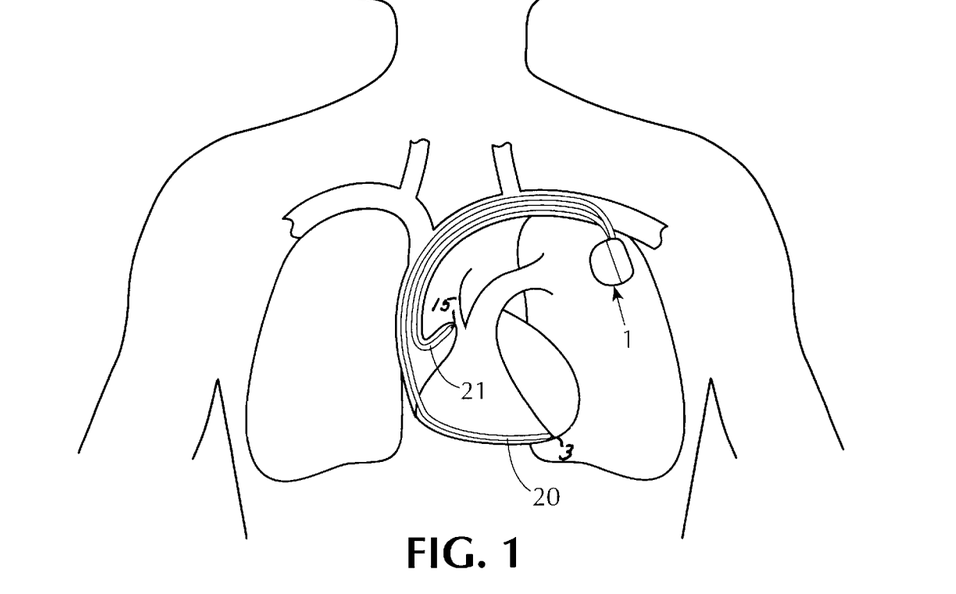
FIG. 1 schematically illustrates a first embodiment of a device in accordance with the invention implanted in a patient.

Referring to FIG. 1, the implementable device for long-term monitoring of congestive heart failure (CHF) includes a signal generator 1, such as a pacemaker pulse generator which is implanted in the patient in any suitable fashion. Typically, the signal generator 1 is located under the skin over the left or right chest in proximity to the subclavian vein.

The implantable device also has a pair of leads 20, 21 which extend from the signal generator 1. As indicated, one lead 20 extends to and is implanted in the right ventricle while the second lead 21 is implanted in the right atrium. As shown, both leads 20, 21 extend from the signal generator 1 through the subclavian vein and superior vena cava to the patient's heart. The one lead 20 has an electrode 3 at the tip or a ring electrode (not shown) while the second lead 21 has an electrode 15 at the tip or a ring electrode (not shown). When current is passed through the leads 20, 21, a first current path or circuit is completed between the electrodes 3 and 15 through the heart tissue and particularly the blood in the venous system. In addition, a second current path extends from the electrode 3 to an electrode (not shown) on the housing of the signal generator 1 with this current path passing through the lung of the patient.

Figure 2:
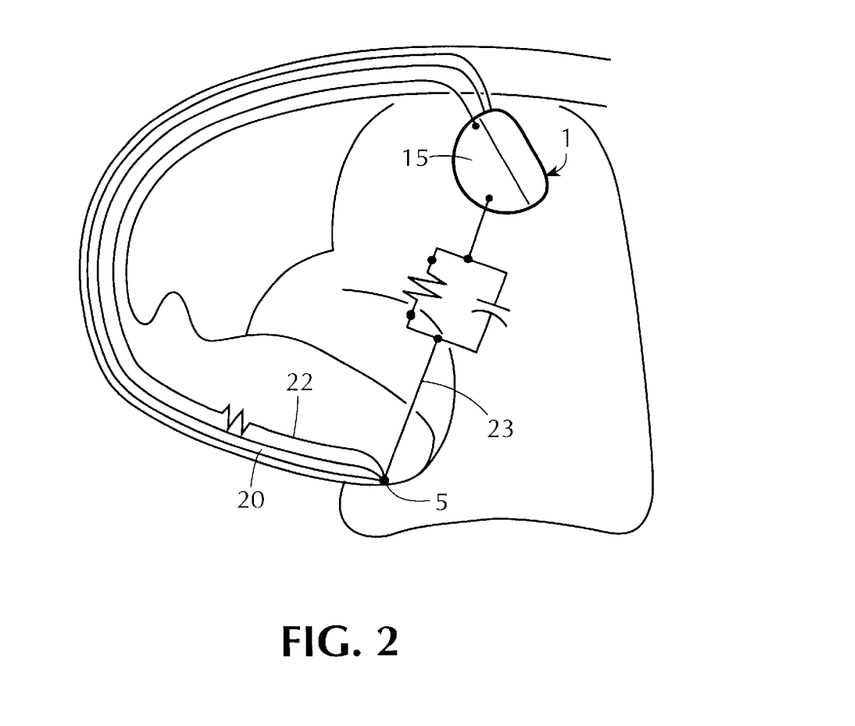
FIG. 2 illustrates a simplified second embodiment with an electrical schematic of the electrical paths.

FIG. 2, wherein like reference characters indicate like parts as above, shows a simplified version of an implantable device with only one lead 20, with an indication of two current paths 22, 23 between the tip of the one lead 20 and a metal housing of the signal generator 1. One current path 22 extends from an electrode 3 at the tip of the lead 20 to an electrode 15 on the metal housing of the signal generator 1 and passes through the blood of the systemic venous system from the right ventricle to the subclavian vein. This is a low resistance path, and with direct current or at low frequencies, most of the current would take this path through the body. Congestion of the systemic venous system would lower this resistance.

The other current path 23 extends from an electrode 3 near the tip of the lead 20 to a second electrode 15 on the housing of the signal generator 1 and passes through the lung tissue. This is a relatively high resistance path with direct current or at low frequencies. This is because the lung is composed mostly of air filled sacs called alveoli. However, at high frequencies, the alveoli act as a multitude of tiny capacitors, whose impedance falls at higher and higher frequencies of alternating current. Thus, with signals containing high frequencies, the capacitive impedance to current flow is low. Therefore, a dual frequency measurement can separate out the systemic venous and the pulmonary (lung) impedance. Alternately, computation of the real and complex components of impedance or admittance at a single high frequency will also separate systemic venous resistance and pulmonary complex impedance, admittance and capacitance. As these tissues get congested, their resistance and impedance will change and allow separate detection of systemic venous and pulmonary congestion.

Figure 3:
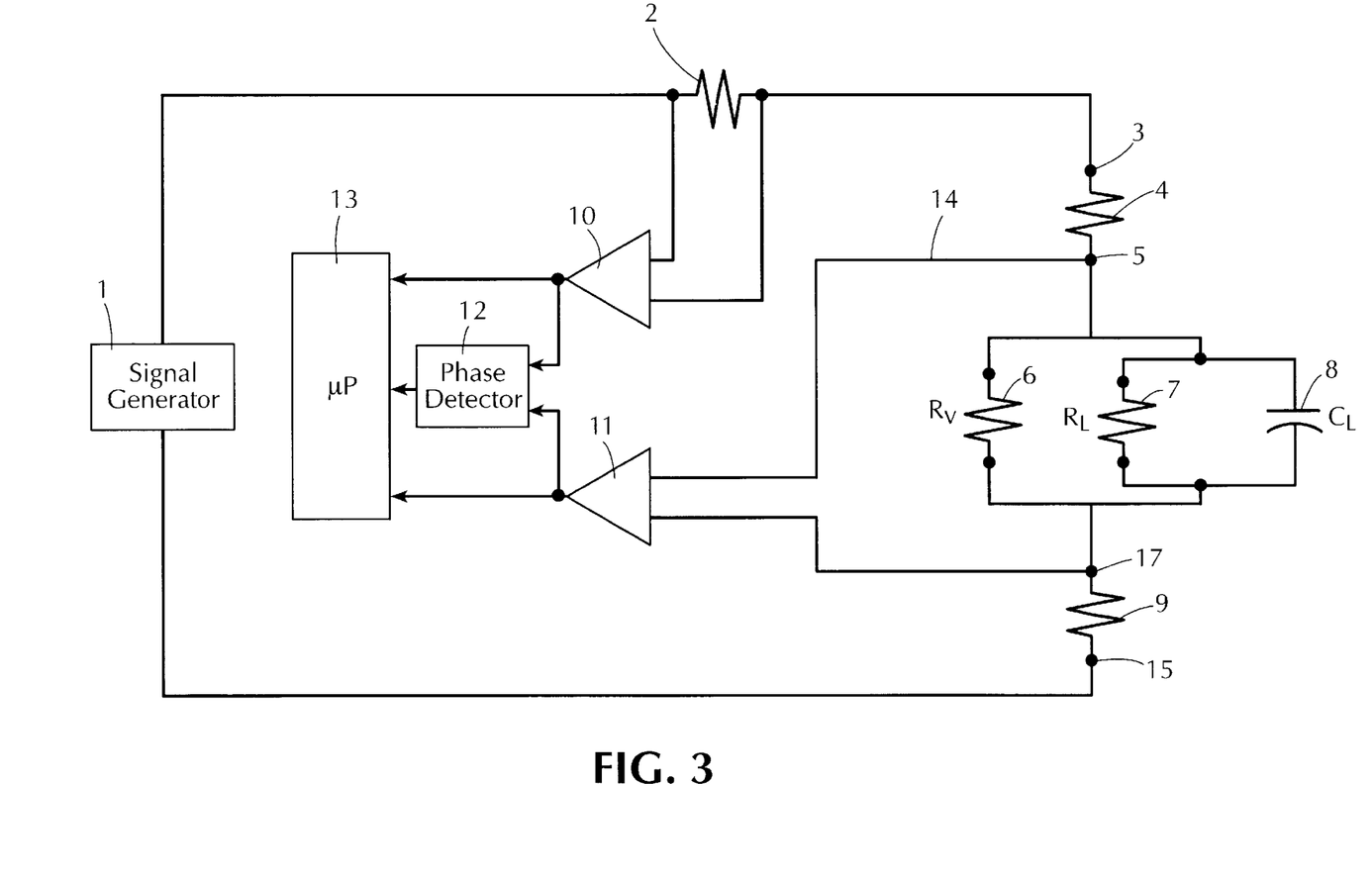
FIG. 3 illustrates a schematic block diagram of the device of FIG. 2 in accordance with the invention.

FIG. 3 shows a block diagram of the device of FIG. 2 as a simplified model.

During operation, the signal generator 1 can produce a constant current or constant voltage signal in the form of a square wave pulse of various widths, a sine wave, a series of alternating square waves, or any signal whose frequency content can be varied to one or more frequencies.

The current flows through a current measuring resistor 2 to the electrode 3 of the lead 20. One, two or more electrodes can be on each lead or on the housing of the generator 1. In any case, the current flows through the electrode-tissue interface as represented by the resistance 4 and then through the systemic venous system as represented by the resistance 6 ($R_v$). The current also flows in parallel through the lung as represented by a resistance 7 ($R_1$) and a capacitor 8 ($C_L$).

The current then flows through the electrode-tissue interface as represented by the resistance 9 and thence to the electrode 15 on the housing of the signal generator 1 to complete the circuit to the signal generator 1.

A means in the form of a microprocessor is provided for measuring the resistance (or conductance) of the current in the path extending through the blood of the systemic venous system as well as at least one of complex impedance, complex admittance and capacitance. This means also includes a means to measure the voltage across the current measuring resistor 2 and to emit a signal indicating the current in the body tissues to an operational amplifier 10 which, in turn, amplifies and delivers the signal to the microprocessor 13 for processing.

The measuring means also employs a second pair of electrodes 5, 17 to pick up the voltage generated by the current through the body tissues and to generate a signal indicative of the voltage. This voltage is amplified and conditioned by an operational amplifier 11 and delivered to the microprocessor 13 for processing.

The measuring means also includes a phase detector 12 which is electrically connected to the two amplifiers 10, 11 to measure the phase angle between the measured current and the measured voltage and to deliver a corresponding signal to the microprocessor 13. The outputs of the two operational amplifiers 10, 11 and the phase detector 12 allow the microprocessor 13 to measure the impedance of the body tissues.

In a multiple frequency embodiment, the impedance is measured using signals generated at two or more frequencies. A DC or a low frequency measurement will reflect systemic venous congestion, while the high frequency measurement of pulmonary capacitive impedance will reflect pulmonary congestion.

The housing of the signal generator 1 also houses the resistor 2, amplifiers 10, 11, phase detector 12 and microprocessor 13 to form a compact unit.

The method of measuring bioimpedance to assess congestive heart failure using the implanted device employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. Note that resistance is impedance measured using direct current. Unlike direct current (DC) which is totally blocked by capacitors, alternating current (AC) can flow through capacitors. The total amount of "resistance" to alternating current flow is called impedance herein. Thus, AC impedance encompasses both the resistive and capacitive components. Therefore, a single frequency embodiment is also feasible as described.

Although bioimpedance devices have been used in the past, there has never been an application of using impedance measurement of organ specific edema content to separate the presence of right and left sided CHF as proposed here.

The signal generator 1 may generate a direct current (DC) signal (frequency=0 Hz) or a sinusoidal low or high frequency signal. Alternatively, the signal generator 1 may produce a long square wave pulse which is a close approximation to a DC signal, or a train of narrow time width and narrowly spaced square wave pulses (which may have alternating positive and negative polarities) that have a high first harmonic frequency component. The use of varying width and frequency square waves is an adaptation of the technique for pacemakers, which already have circuitry for the generation of signals approximating square waves. A variety of other waveforms may also be used.

The arrangement of the electrodes in the chest may not be critical, since some arrangements may be superior to others. Typically, the right ventricular and right atrial leads 20, 21 have one (unipolar) or two (bipolar) electrodes each at or near the tip of the leads. New pacemaker lead technology also exists to allow lead placement in other areas of the heart, such as the coronary sinus and coronary veins. The metallic housing of the device itself may be used as an electrode since the housing is in contact with the tissues. Additional electrodes can be placed on the surface of the device as well. Electrodes may also be implanted in other ways, such as within subcutaneous tissues around the chest wall or inside the chest as during heart surgery.

The signal generator current is applied to one pair of electrodes 3, 15 while the voltage generated by the current flow through the tissues is detected using the other pair of electrodes 5, 17. Any two arbitrary pairs of electrodes in the body can be chosen for the connections to the signal generator 1.

The impedance at zero frequency (DC) is called resistance. The electrical resistance through the blood path of the venous circulation ($R_v$) is in parallel to the lung, which has a much higher resistance ($R_L$). The electrical law of parallel resistances is that the total resistance ($R_T$) is equal to the "product over the sum", or $(R_v \times R_L)/(R_v+R_L)$. If $R_V$ is much smaller than $R_L$, then the total resistance ($R_T$) will be close to $R_V$. In other words, the systemic venous resistance will dominate the measurement at DC or low frequencies.

Figure 4:
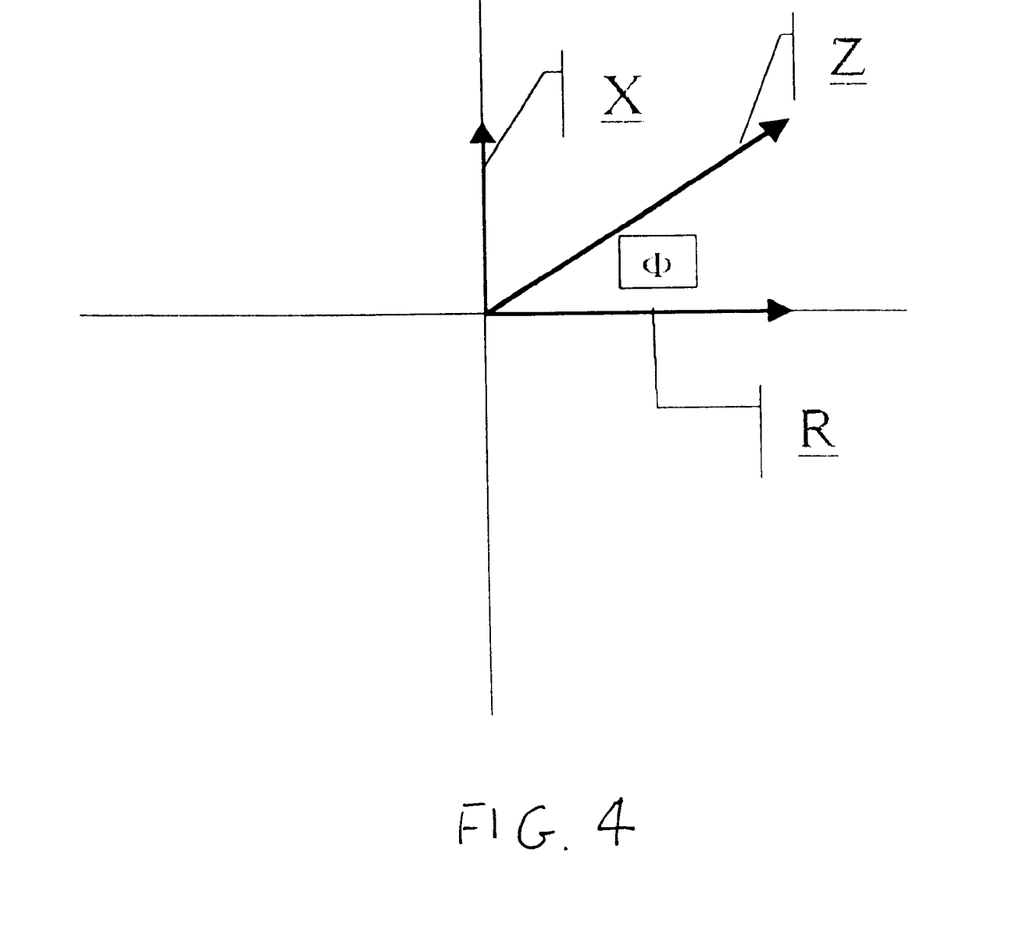
FIG. 4 is a vector diagram for impedance Z.

At DC, capacitive impedance is infinite. That is, DC current does not flow through a capacitor. However, at high frequencies, the presence of capacitance in a circuit causes a phase shift in the relationship between voltage and current. With this phase shift, resistance alone is not considered but rather a combination of resistance and reactance called impedance is considered. Impedance is a vector quantity, which can be graphed as shown in FIG. 4 as the sum of two vectors at night angles to each other. Resistance is the horizontal component, and reactance is the vertical component. The sum of the vectors is impedance. The length of the vector (the scalar magnitude), and the phase angle of the vector describe the relationship between resistance and reactance. The microprocessor 13 of the device computes the magnitude and the phase angle of the impedance. From that, the capacitive reactance can be calculated, and knowing the frequency of the signal, the capacitance can be calculated.
Because the lung is the dominant capacitor in the circuit, a property of the lung is being independently measured to assess congestion in some meaningful way.

Instead of measuring the resistance to current flow in the first path through the systemic venous system, the conductance may be measured. In this respect, conductance is the inverse of resistance. In addition, as an alternative to measuring the impedance, i.e. the complex impedance of the current flow through the lung tissue, complex admittance or capacitance may be measured as an indication of pulmonary congestion. In this respect, admittance is the inverse of impedance. Capacitance and complex impedance ($X_c$) are interrelated according to the frequency (f) by the formula: $X_c = 1/(2\pi f\, C)$ In the embodiment where a single frequency measurement is used, a signal at high frequency is emitted by the signal generator 1. The information provided to the microprocessor 13 from the two amplifiers 10, 11 and the phase detector 12 is then processed to obtain the magnitude and the phase angle of the impedance. The microprocessor 13 is then able to compute the real component of impedance (resistance) which will primarily be due to current flow in the systemic venous system as well as the complex component of impedance (capacitive reactance) which will reflect conditions in the lung. As noted above, the lung will also have a resistive component but this is so high that little current will flow and can be considered clinically negligible. As a result, the microprocessor 13 acts as a means for measuring the resistance (or conductance) to current flow in the blood flow path in the systemic venous system but also measures at least one of complex impedance (capacitive reactance), complex admittance or capacitance in the current path passing through the lung.

Thus, this invention allows separate approximations of systemic venous (right heart) and pulmonary (left sided) congestion. The invention takes advantage of the different electrical properties of blood and of lung tissue.

The invention thus has the potential to assess systemic venous congestion (right heart failure) and pulmonary congestion (left heart failure), both separately and semi-independently. By altering the frequency content of the signal from the signal generator, current flow is encouraged through the systemic venous system at DC while at high frequencies, enhanced current flow is encouraged in the lung.

As is known, measurements of venous congestion will be affected by the position of the body. Thus, the measurement of systemic venous congestion can be confounded by body position. Most modern pacemakers contain a single accelerometer in the coronal plane which is used to measure forward and backward changes in velocity, i.e. acceleration, of the body as one walks about or moves. The signals generated by the accelerometer are a gross measure of "activity" and are used to speed up the pacemaker's rate to produce an approximation of physiological heart rate response.

The measurement device of the invention may be used with accelerometer devices which are conventionally used to determine the activity of a patient. By using accelerometers to sense the direction of gravitational acceleration, an array of three orthogonally positioned accelerometers can determine if a patient is lying on his back, on his stomach, on his left side, on his right side, standing or sitting erect, or even upside down. With two accelerometers, one in the coronal plane and one in the sagittal plane, one would know all these positions except whether the patient were erect or upside down. Usually, two accelerometers should be adequate. Likewise, one sensor in the coronal plane would be sufficient if interest is only for the prone or supine positions.

The conventional activity sensing function of an accelerometer is also helpful in acquiring reproducible measurements. Body activity will increase cardiac output and also change the amount of blood in the systemic venous system or lungs. Measurements of congestion may be most reproducible when body activity is at a minimum and the patient is at rest. Thus, the use of an accelerometer allows one to sense both body position and body activity.

Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. All comparative measurements should be made under the same activity conditions.

Two other variables will also need to be controlled to permit reproducible measurements, i.e. variations of the cardiac cycle and variations in the respiratory cycle. As is known, the ventricles are at their most compliant during diastole. The end of the diastolic period is marked by the QRS on the electrocardiographic means (EKG) for monitoring the cardiac cycle. It is also known that nearly all pacemakers are able to detect the QRS using sensing amplifiers connected to the right ventricular lead. Thus, it would be a simple matter to time the measurements of impedance to diastole using the sensed QRS as a reference point.

Respiratory variation also has significant effects on the amount of blood in the central venous system and creates undesirable variability in systemic venous blood volume measurements. Respiratory variation in impedance is used by many pacemakers to monitor respiratory rate and volume. As the lungs fill with air during inspiration, impedance increases, and during expiration, impedance decreases. Most conveniently, impedance should be measured during expiration to minimize the effect of breathing on central systemic venous volume.

While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation.

The invention provides a device that can detect congestive heart failure (CHF) in early stages and alert a patient to prevent disabling and even lethal episodes of CHF. Early treatment can avert progression of the disorder to a dangerous stage. Standard clinical methods such as daily patient weight measurements to detect water retention are often unreliable and subject to patient noncompliance. An early warning alarm for a patient to take action would be of tremendous importance.

The invention further provides a device which could be a stand-alone implanted unit, or can be incorporated into an implantable pacemaker or cardioverter/defibrillator. Ultimately, such an early warning device could be coupled to a drug pump, which can automatically deliver diuretic or other therapies on an as needed basis.

What is claimed is:

1. An implantable device for long term monitoring of congestive heart failure comprising
   a first electrode for implanting in a right heart of a patient;
   a second electrode for implanting in the patient;

a signal generator for emitting an electrical signal from said first electrode to said second electrode through at least a first current path extending through the blood of a systemic venous system of the patient and through a second current path extending through a lung of a patient; and means for measuring at least one of systemic venous congestion and pulmonary congestion whereby changes in the resistance and conductance of current in said first current path are indicative of said systemic venous congestion and changes in at least one of complex impedance, complex admittance and capacitance in said second current path over a period of time are indicative of said pulmonary congestion.

2. An implantable device as set forth in claim 1 wherein said means for measuring includes a current measuring resistor for measuring the current passing between said signal generator and said first electrode and an operational amplifier for measuring the voltage across said resistor and emitting a responsive signal indicating the current measured.

3. An implantable device as set forth in claim 2 wherein said means for measuring further includes a pair of electrodes for implanting in the patient for measuring the voltage generated by said signal in said current paths and a second operational amplifier for amplifying the measurement of voltage from said current paths.

4. An implantable device as set forth in claim 3 wherein said means for measuring further includes a phase detector connected to each said amplifier to measure the phase angle between the measured voltage and the indicated current in said resistor, and a microprocessor electrically connected to said phase detector and to each said amplifier to receive values corresponding to the measured phase angle, the detected voltage and the indicated current and to measure the impedance of the body tissues based on said received values.

5. An implantable device as set forth in claim 1 wherein said signal is a direct current signal.

6. An implantable device as set forth in claim 1 wherein said signal has a low frequency sufficient to encourage transmission through a central systemic venous system.

7. An implantable device as set forth in claim 1 wherein said signal has a high frequency to permit transmission through a lung.

8. An implantable device as set forth in claim 1 wherein said means for measuring measures the magnitude and phase angle of impedance and calculates a real component of said impedance as an indication of congestion in the systemic venous system and a complex component of said impedance as an indication of congestion in the lung.

9. An implantable device for long term monitoring of congestive heart failure comprising a signal generator for generating an electrical signal at least two different frequencies;

a current measuring resistor electrically connected to said signal generator for passage of said electrical signal therethrough;

a first electrode connected to said resistor for implanting in a right ventricle of a patient to deliver said signal through a first current path extending from the right ventricle through the blood of a systemic venous system and subclavian vein of the patient and to a second path extending through a lung of the patient;

a second electrode for implanting in a right atrium of the patient and connected to said signal generator to complete a circuit with said first electrode to said signal generator;

a first operational amplifier for measuring the voltage across said resistor and emitting a signal indicative of the current flowing through said resistor;

a pair of electrodes for implanting in the patient for detecting the voltage generated by said signal through the body tissue of the patient;

a second operational amplifier connected to said pair of electrodes to amplify the detected voltage;

a phase detector connected to each said amplifier to measure a phase angle between the detected voltage and the indicated current in said resistor; and a microprocessor connected to said phase detector and to each said amplifier to receive values corresponding to the measured phase angle, the detected voltage and the indicated current and to calculate the impedance of the body tissues based on said received values whereby a calculated resistance or conductance at DC or a calculated impedance at a lower frequency of said electrical signal from said signal generator is indicative of systemic venous congestion and a calculated complex impedance at a higher frequency of said electrical signal from said signal generator is indicative of pulmonary congestion.

10. An implantable device as set forth in claim 9 wherein one of said signals is a direct current signal.

11. An implantable device as set forth in claim 9 wherein said means for measuring measures the magnitude and phase angle of impedance and calculates a real component of said impedance as an indication of congestion in the systemic venous system and a complex component of said impedance as an indication of congestion in the lung.

12. In combination an implantable device having at least a first electrode for implanting in a right heart of a patient; at least a second electrode for implanting in the patient; a signal generator for emitting an electrical signal from said first electrode to said second electrode through at least a first current path extending through the blood of a systemic venous system of the patient and through a second current path extending through a lung of a patient; and means for measuring at least one of systemic venous congestion and pulmonary congestion whereby changes in the resistance and conductance of current in said first current path are indicative of said systemic venous congestion and changes in at least one of complex impedance, complex admittance and capacitance in said second current path over a period of time are indicative of said pulmonary congestion; and an accelerometer for sensing a direction of gravitational acceleration as an indication of patient position and for sensing body activity for correlation with a measurement of congestion from said implantable device.

13. The combination as set forth in claim 12 further comprising means for monitoring the respiratory rate, respiratory cycle and volume of the patient for correlation with a measurement of congestion from said implantable device.

14. In combination an implantable device having at least a first electrode for implanting in a right heart of a patient; at least a second electrode for implanting in the patient; a signal generator for emitting an electrical signal from said first electrode to said second electrode through at least a first current path extending through the blood of a systemic venous system of the patient and through a second current path extending through a lung of a patient; and means for measuring at least one of systemic venous congestion and pulmonary congestion whereby changes in the resistance and conductance of current in said first current path are indicative of said systemic venous congestion and changes in at least one of complex impedance, complex admittance and capacitance in said second current path over a period of time are indicative of said pulmonary congestion; and an electrocardiogram for measuring variations in a cardiac cycle for correlation with a measurement of congestion from said implantable device.

15. A method of measuring bioimpedance to assess congestive heart failure comprising the steps of passing a electrical signal of high frequency into a first path extending through a systemic venous system from a right ventricle to a subclavian vein of a patient; and a second path electrically parallel to said first path and extending through a lung of the patient;

measuring the resistance to current flow of said signal in said first path whereby a decrease in measured resistance is indicative of congestion of the venous system; and measuring the capacitive impedance or admittance to current flow of said signal in said second path whereby a change in measured capacitive impedance or admittance is indicative of congestion of the lung.

16. A method as set forth in claim 15 which further comprises the steps of measuring the magnitude of impedance to said signal in said paths and the phase angle of said impedance;

obtaining the real component of said impedance as a measure of the resistance to current flow in said first path; and obtaining the complex component of said impedance as a measure of capacitive reactance in said second path.

17. In combination an implantable device for long term monitoring of congestive heart failure comprising a first electrode for implanting in a right heart of a patient, a second electrode for implanting in the patient, a signal generator for emitting a signal from said first electrode to said second electrode through at least one of a current path extending through the blood of a systemic venous system and through a second current path extending through a lung of a patient, and means for measuring changes in impedance in at least one of the systemic venous system and the lung as a measure of at least one of systemic venous congestion and pulmonary congestion;

an accelerometer for sensing gravitational acceleration as an indication of patient position;

means for monitoring the respiratory cycle of the patient; and electrocardiographic means for monitoring the cardiac cycle of the patient whereby measurements of impedance made during particular phases of said respiratory cycle and said cardiac cycle and at reproducible body positions are indicative of the degree of congestion of the patient.

18. The combination as set forth in claim 17 wherein said means for measuring changes in impedance measures the magnitude and phase angle of impedance and calculates a real component of said impedance as an indication of systemic venous congestion and a complex component of said impedance as an indication of pulmonary congestion.

19. In combination an implantable device for long term monitoring of congestive heart failure comprising a first electrode for implanting in a right heart of a patient, a second electrode for implanting in the patient, a signal generator for emitting a signal from said first electrode to said second electrode through at least one of a current path extending through the blood of a systemic venous system and through a second current path extending through a lung of a patient, means for measuring changes in impedance in at least one of the systemic venous system and the lung as a measure of at least one of systemic venous congestion and pulmonary congestion;

an accelerometer for sensing gravitational acceleration as an indication of patient position; and electrocardiographic means for monitoring the cardiac cycle of the patient whereby measurements of impedance made during particular phases of said cardiac cycle and at reproducible body positions are indicative of the degree of congestion of the patient.

20. In combination an implantable device for long term monitoring of congestive heart failure comprising a first electrode for implanting in a right heart of a patient, a second electrode for implanting in the patient, a signal generator for emitting a signal from said first electrode to said second electrode through at least one of a current path extending through the blood of a systemic venous system and through a second current path extending through a lung of a patient, means for measuring changes in impedance in at least one of the systemic venous system and the lung as a measure of at least one of systemic venous congestion and pulmonary congestion;

an accelerometer for sensing gravitational acceleration as an indication of patient position; and means for monitoring the respiratory cycle of the patient whereby measurements of impedance made during particular phases of said respiratory cycle and at reproducible body positions are indicative of the degree of congestion of the patient.

* * * * *

UNITED STATES PATENT AND TRADEMARK OFFICE
CERTIFICATE OF CORRECTION

PATENT NO. : 6,473,640 B1
DATED : October 29, 2002
INVENTOR(S) : Jay Erlebacher

It is certified that error appears in the above-identified patent and that said Letters Patent is hereby corrected as shown below:

Column 1,
Line 18, cancel "of" (second occurrence)
Line 18, cancel "."

Column 8,
Line 57, change "night" to -- right --

Signed and Sealed this

Fourth Day of February, 2003

JAMES E. ROGAN
*Director of the United States Patent and Trademark Office*